United States Patent [19]

Wei et al.

[11] Patent Number: 5,422,411
[45] Date of Patent: Jun. 6, 1995

[54] TRIFLUOROSTYRENE AND SUBSTITUTED TRIFLUOROSTYRENE COPOLYMERIC COMPOSITIONS AND ION-EXCHANGE MEMBRANES FORMED THEREFROM

[75] Inventors: Jinzhu Wei, Burnaby; Charles Stone, Vancouver; Alfred E. Steck, West Vancouver, all of Canada

[73] Assignee: Ballard Power Systems Inc., Vancouver, Canada

[21] Appl. No.: 124,924

[22] Filed: Sep. 21, 1993

[51] Int. Cl.$^6$ .................... C08F 14/18; C08J 5/22
[52] U.S. Cl. .................... 526/243; 521/27; 521/32; 521/33; 526/242; 526/247; 526/248; 526/249; 526/291; 526/292.8; 526/292.9; 526/292.95
[58] Field of Search .................. 521/33, 37, 27; 526/243

[56] References Cited

U.S. PATENT DOCUMENTS

| | | |
|---|---|---|
| 2,651,627 | 2/1950 | Prober . |
| 3,282,875 | 11/1966 | Connolly et al. . |
| 3,341,366 | 9/1967 | Hodgdon, Jr. ............ 429/33 |
| 3,528,858 | 9/1970 | Hodgdon, Jr. et al. . |
| 4,012,303 | 3/1977 | D'Agostino et al. . |
| 4,330,654 | 5/1982 | Ezell et al. . |
| 4,605,685 | 8/1986 | Momose et al. . |

FOREIGN PATENT DOCUMENTS

| | | |
|---|---|---|
| 53-26884 | 3/1978 | Japan . |
| 3-27053 | 2/1991 | Japan . |
| 327053 | 2/1991 | Japan . |

OTHER PUBLICATIONS

"Palladium-Catalyzed Cross-Coupling of Perfluoroalkenylzine Reagents with Aryl Iodides. A New, Simple Synthesis of $\alpha,\beta,\beta$-Trifluorostyrenes and the Stereoselective Preparation of 1-Arylperfluoropropenes", *J. Org. Chem.*, vol. 53, pp. 2714–2720, (1988).

"$\alpha\beta\beta$-Trifluorostyrene and polymers based on it", *Russian Chemical Reviews*, vol. 59, pp. 575–589, (1990).

*Primary Examiner*—Fred Zitomer
*Attorney, Agent, or Firm*—McAndrews, Held & Malloy, Ltd.

[57] ABSTRACT

Polymeric compositions are derived from copolymers of $\alpha,\beta,\beta$-trifluorostyrene with a variety of substituted $\alpha,\beta,\beta$-trifluorostyrenes. These compositions are suitable for use as membranes, particularly as ion-exchange membranes, and most particularly as solid polymer electrolytes in electrochemical applications, such as, for example, electrochemical fuel cells.

8 Claims, 1 Drawing Sheet

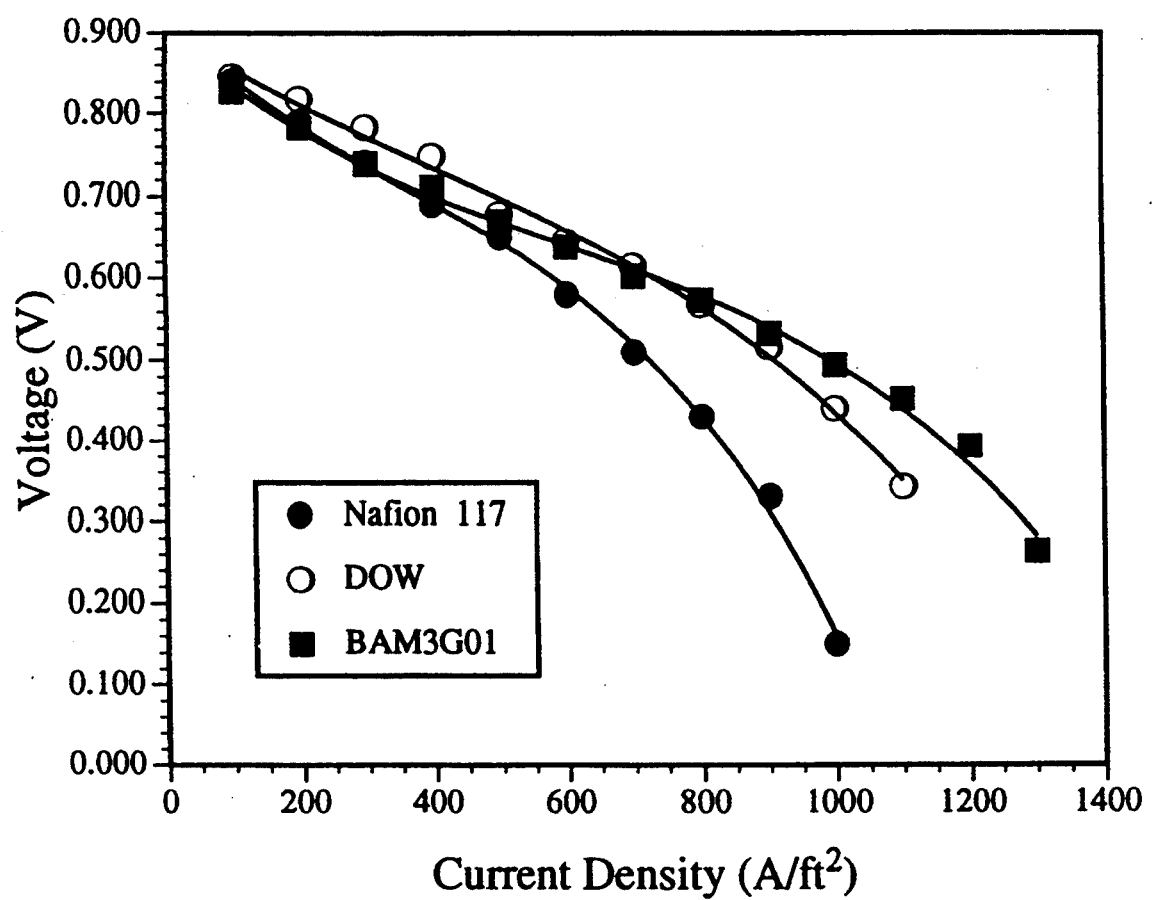

TRIFLUOROSTYRENE AND SUBSTITUTED TRIFLUOROSTYRENE COPOLYMERIC COMPOSITIONS AND ION-EXCHANGE MEMBRANES FORMED THEREFROM

FIELD OF THE INVENTION

The present invention relates to trifluorostyrene based polymeric compositions. More particularly, the present invention relates to polymeric compositions derived from copolymers of $\alpha,\beta,\beta$-trifluorostyrene with a variety of substituted $\alpha,\beta,\beta$-trifluorostyrenes. These compositions are particularly suitable for use as solid polymer electrolytes in electrochemical applications, such as, for example, electrochemical fuel cells.

BACKGROUND OF THE INVENTION

A variety of membranes have been developed over the years for application as solid polymer electrolytes for fuel cells and other electrochemical applications. These polymers have typically been perfluorinated aliphatic compositions, such as those described in U.S. Pat. Nos. 3,282,875 and 4,330,654. These compositions are very expensive membranes, and in the case of the '875 patent tend to exhibit poor fuel cell performance characteristic at high current densities. Alternatively, a series of low-cost polyaromatic-based systems have been investigated, such as those described in U.S. Pat. Nos. 3,528,858 and 3,226,361. These materials suffer from poor chemical resistance and mechanical properties which tend to limit their use in fuel cell applications. The investigation of other materials has involved the study of polymers containing the monomer unit $\alpha,\beta,\beta$-trifluorostyrene, for example, those described in U.S. Pat. No. 3,341,366 and Japanese Unexamined Patent Publication (Kokai) No. 53-26884. However, these compositions suffered from poor mechanical properties in the case of the '366 patent, and very low polymer yield in the case of the Japanese patent publication.

It is therefore an object of the invention to produce, in high yield, a low-cost ion-exchange polymer membrane with favorable chemical and mechanical properties.

It is also an object of the invention to produce an ion-exchange polymer membrane that is suitable for use in a wide variety of applications, including electrochemical applications such as fuel cells.

SUMMARY OF THE INVENTION

The above and other objects are achieved by a polymeric composition including:

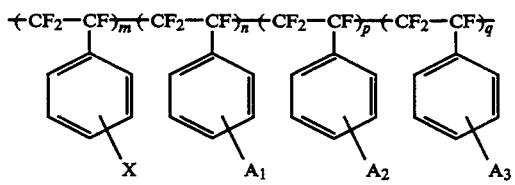

where at least two of m, n, p and q are integers greater than zero; $A_1$, $A_2$ and $A_3$ are selected from the group consisting of alkyls, halogens, $C_yF_{2y+1}$ where y is an integer greater than zero, O-R (where R is selected from the group consisting of alkyls, perfluoroalkyls and aryls), $CF=CF_2$, CN, $NO_2$ and OH; and X is selected from the group consisting of $SO_3H$, $PO_2H_2$, $PO_3H_2$, $CH_2PO_3H_2$, COOH, $OSO_3H$, $OPO_3H_2$, $OArSO_3H$ where Ar is an aromatic, $NR_3^+$ (where R is selected from the group consisting of alkyls, perfluoroalkyls and aryls), and $CH_2NR_3^+$ (where R is selected from the group consisting of alkyls, perfluoroalkyls and aryls). The $A_1$, $A_2$, $A_3$ and X substituents may be located in the ortho, meta and/or para positions. The copolymer may also be binary, ternary or quaternary.

The $A_1$, $A_2$ and $A_3$ substituents may be further elaborated by known means such as, for example, by hydrolysis of the CN group to form COOH or by reduction with common reducing agents (such as, for example, Raney nickel) to form a primary amine, thereby transforming the $A_1$, $A_2$ and $A_3$ substituents into further "X"-type ion-exchange moieties. The resulting polymeric composition may thus comprise one or more type of ion-exchange moiety, and may also comprise both cation and anion exchange moieties.

The polymeric composition can also consist essentially of the above chemical units.

At least some of the adjacent polymers are preferably crosslinked for applications in which the resulting polymeric membrane should retard swelling.

The polymeric composition in which m and n are integers greater than zero, p and q are both zero, $A_1$ is fluorine or $CF_3$, and X is $SO_3H$, is suitably formed into a membrane, and is preferably employed as an ion-exchange membrane, most preferably as a cation exchange membrane in an electrochemical fuel cell.

BRIEF DESCRIPTION OF THE DRAWINGS

FIG. 1 is a plot of voltage as a function of current density in an electrochemical fuel cell employing, respectively, a Nafion 117 (DuPont's trade designation) cation exchange membrane, a Dow experimental cation exchange membrane, and a sulfonated $\alpha,\beta,\beta$-trifluorostyrene copolymeric membrane.

DETAILED DESCRIPTION OF THE PREFERRED EMBODIMENTS

The polymeric compositions of the present invention are produced by reacting mixtures of $\alpha,\beta,\beta$-trifluorostyrene having the following chemical formula:

where m is an integer greater than zero, with other monomer(s) selected from a group of substituted $\alpha,\beta,\beta$-trifluorostyrenes having the following chemical formula:

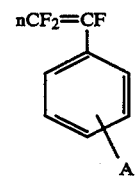

where n is an integer greater than zero and A is selected from the group consisting of alkyls, halogens, $C_yF_{2y+1}$ where y is an integer greater than zero, O-R (where R is selected from the group consisting of alkyls, perfluoroalkyls and aryls), CF=CF$_2$, CN, NO$_2$ and OH, to form a base copolymer. The "A" substituent may be located in the ortho, meta and/or para positions.

The above monomers are mixed in an aqueous medium containing a free radical initiator and an emulsifying agent, at temperatures in the range of about 35° C.–95° C. for a time period of about 24 to 74 hours under an inert atmosphere. The base copolymers can be sulfonated, or in accordance with a further aspect of this invention, may be phosphorylated, carboxylated, quaternary-aminoalkylated or chloromethylated, and further modified to yield —CH$_2$PO$_3$H$_2$, —CH$_2$NR$_3^+$ where R is an alkyl, or —CH$_2$NAr$_3^+$ where Ar is an aromatic (arene), to provide a cation or anion exchange membrane. Further still, the aromatic moiety may contain a hydroxyl group which can be readily elaborated by existing methods to generate —OSO$_3$H and —OPO$_3$H$_2$ cationic exchange sites on the polymer.

In a typical sulfonation reaction used to produce a cationic exchange membrane, the copolymer is dissolved in an appropriate solvent and then reacted with a sulfonating reagent, such as chlorosulfonic acid or a Lewis acid-base complex of sulfur trioxide. The solvent for such a reaction can be selected from the class consisting of chlorinated aliphatic hydrocarbons, such as dichloroethane, tetrachloroethylene and chloroform. The copolymer solution is rendered completely homogeneous prior to the addition of the solution containing the sulfonating reagent. The reaction is then run within the temperature range from about 18° C. plus or minus 5° C., up to the boiling point of the solvent. To ensure adequate functionalization of the copolymer, the reaction is allowed to continue for a period of about one to about four hours, or longer.

The copolymers thus prepared possess favorable properties, such as high heat stability, chemical resistance and favorable mechanical properties, such as tensile strength, compared to the homopolymeric material formed from α,β,β-trifluorostyrene (TFS) alone.

The following examples are for purposes of illustration and are not intended to limit the invention. Examples 1–9 describe the synthesis of base copolymers. Examples 10–21 describe the sulfonation of the base copolymers synthesized in Examples 1–9. Example 22 sets forth the results of tests performed on three ion-exchange copolymer membranes formed from the sulfonated copolymers of the present invention, in an electrochemical fuel cell.

Examples 1–4 set forth the preparation of the following base copolymer:

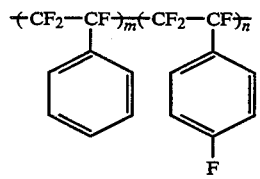

where m and n are integers greater than zero.

EXAMPLE 1

352 mL of deionized water and 7.05 g of dodecylamine hydrochloride were placed in a 500 mL, three-necked round bottomed flask equipped with a mechanical stirrer and a reflux condenser. N$_2$ was passed through the reaction system to replace O$_2$ for about ½ hour. A charge of 44.4 g (0.28 mole, 80%) of α,β,β-trifluorostyrene (TFS) and 12.4 g (0.07 mole, 20%) of p-fluoro-α,β,β-trifluorostyrene (p-F-TFS) was added into the flask. The resulting emulsion was stirred and heated to 50° C. and then 0.53 g of potassium persulfate was added into the reaction system running for a period of 48 hours. Upon completion of the reaction, the polymer emulsion was poured into a 2 L beaker containing an aqueous NaOH solution (the molar ratio of NaOH/dodecylamine hydrochloride was 5:1) and boiled for one hour to destroy the emulsifier. The mixture was filtered and the copolymer was transferred into another beaker containing methanol and stirred for 2 hours. After filtration the copolymer was redissolved in toluene and slowly precipitated in methanol. A white, fibrous copolymer was obtained and dried in a vacuum oven at 70° C., 30 Torr for several hours. The copolymerization yield was 43.3 g (76.2%) and the intrinsic viscosity ([η]) of the copolymer was 1.58 dL/g as determined in toluene at 30° C.

EXAMPLE 2

The same procedure was employed as in Example 1, except that 200 mL of deionized water, 4.00 g of dodecylamine hydrochloride, 25.2 g of TFS (80%), 7.04 g of p-F-TFS (20%) and 0.30 g of potassium persulfate were used in the copolymerization. The yield was 21.8 g (67.6%) and the [η] of the copolymer was 1.56 dL/g.

EXAMPLE 3

200 mL of deionized water and 4.0 g of dodecylamine hydrochloride were placed in a 500 mL, three-necked round bottomed flask equipped with a mechanical stirrer and a reflux condenser. N$_2$ was passed through the reaction system to replace O$_2$ for about ½ hour. A charge of 25.2 g (0.16 mole, 80%) of TFS, 7.04 g (0.04 mole, 20%) of p-F-TFS and 0.30 g of potassium persulfate was added into the reaction flask. The resulting emulsion was stirred and heated at 50° C. for a period of 48 hours. On completion of the reaction, the polymer emulsion was poured into a 2 L beaker containing an aqueous NaOH solution (the molar ratio of NaOH/dodecylamine hydrochloride was 5:1) and boiled for one hour to destroy the emulsifier. The mixture was filtered and the copolymer was transferred into another beaker containing methanol and stirred for a couple of hours. After filtration the copolymer was redissolved in toluene and slowly precipitated in methanol. A white, fibrous copolymer was obtained and dried in a vacuum oven at 70° C., 30 Torr for several hours. The yield was 20.1 g (62.3%) and the [η] of the copolymer was 1.12 dL/g.

EXAMPLE 4

The same procedure was employed as in Example 3, except that the reaction was run for 72 hours instead of 48 hours. The yield was 18.5 g (57.5%) and the [η] of the copolymer was 1.12 dL/g.

Examples 5–8 set forth the preparation of the following base copolymer:

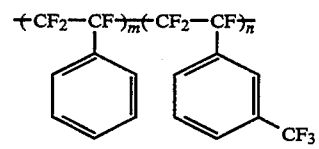

EXAMPLE 5

The same procedure was employed as in Example 1, except that 237 mL of deionized water, 4.73 g of dodecylamine hydrochloride, 29.8 g of TFS (80%), 10.7 g of m-CF$_3$-TFS (20%) and 0.35 g of potassium persulfate were used in the copolymerization. The yield was 29.7 g (73.4%) and the [$\eta$] of the copolymer was 1.16 dL/g.

EXAMPLE 6

The same procedure was employed as in Example 3, except that 25.2 g of TFS (80%), 9.0 g of m-CF$_3$-TFS (20%) were used and the reaction was run for 72 hours instead of 48 hours. The yield was 19.0 g (55.5%) and the [$\eta$] of the copolymer was 1.07 dL/g.

EXAMPLE 7

The same procedure was employed as in Example 1, except that 686 mL of deionized water, 12.7 g of dodecylamine hydrochloride, 80.0 g of TFS (80%), 28.7 g of m-CF$_3$-TFS (20%) and 0.95 g of potassium persulfate were used and the polymerization was run for 72 hours. The yield was 91.6 g (84.3%) and the [$\eta$] of the copolymer was 1.28 dL/g. The $^{19}$F-NMR analysis of this copolymer was performed on a VARIAN XL-300 NMR instrument using CDCl$_3$ as solvent. The results indicate that the copolymer obtained contains 27% of the m-CF$_3$-TFS monomer unit.

EXAMPLE 8

The same procedure was employed as in Example 1, except that 725 mL of deionized water, 14.5 g of dodecylamine hydrochloride, 79.9 g of TFS (70%), 48.9 g of m-CF$_3$-TFS (30%) and 1.09 g of potassium persulfate were used and the polymerization was run for 72 hours. The yield was 105.1 g (81.6%) and the [$\eta$] of the copolymer was 1.37 dL/g. The $^{19}$F-NMR analysis has shown that the copolymer contains 38% of m-CF$_3$-TFS monomer unit.

EXAMPLE 9

The same procedure was employed as in Example 1, except that 189 mL of deionized water, 3.77 g of dodecylamine hydrochloride, 17.8 g of TFS (60%), 17.0 g of m-CF$_3$-TFS (40%) and 0.28 g of potassium persulfate were used and the polymerization was run for 72 hours. The yield was 28.0 g (80.5%) and the [$\eta$] of the copolymer was 1.67 dL/g. The m-CF$_3$-TFS monomer unit content in the copolymer was 45% as determined by $^{19}$F-NMR.

Examples 10 and 11 set forth the preparation of the following sulfonated copolymer:

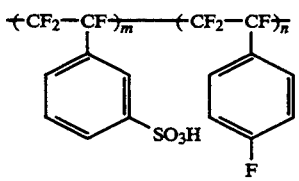

EXAMPLE 10

A solution of 6.17 mL of ClSO$_3$H in 50 mL chloroform was added into a three necked flask containing a solution of 7.5 g of TFS-p-F-TFS copolymer (20% p-F-TFS) in 400 mL of chloroform over 5 minutes. The molar ratio of ClSO$_3$H/monomer unit was 2:1. The reaction was run at 60° C. for 4 hours. The reaction mixture was then transferred into 5 L of deionized water, boiled for one hour, filtered and the product was dried in a vacuum oven at 50° C. and 30 Torr. The yield was 8.8 g and the equivalent weight and water content of the sulfonated copolymer were 586 g/mol and 40%, respectively.

EXAMPLE 11

7.5 g of TFS-p-F-TFS copolymer (20% p-F-TFS) was dissolved in 169 mL of chloroform in a three necked flask fitted with a dropping funnel, a thermocouple and an mechanical stirrer. A SO$_3$/O=P(OEt)$_3$ complex was made by adding 10.12 mL of O=P(OEt)$_3$ and 9.86 mL of SO$_3$ into 49.8 mL of chloroform at 0° C. The SO$_3$/O=P(OEt)$_3$ molar ratio was 4:1 and the SO$_3$/monomer unit molar ratio was 5.3:1. This complex was immediately transferred to a dropping funnel and added to the mixture over 10 minutes. The reaction was stirred at 60° C. for 4 hours. The same workup procedure was used as described in Example 10. The yield was 11.4 g and the equivalent weight and water content of the sulfonated copolymer were 350 g/mol and 260%, respectively.

Examples 12–21 set forth the preparation of the following sulfonated copolymer:

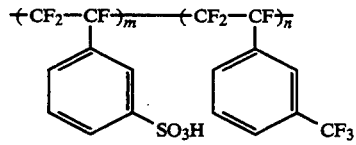

EXAMPLE 12

The same procedure was employed as in Example 11, except that an SO$_3$/O=P(OEt)$_3$ complex containing 3.97 mL of O=P(OEt)$_3$ and 3.77 mL of SO$_3$ in 19.4 mL of chloroform was added rapidly into the reaction system, the molar ratio of SO$_3$/monomer unit was 2:1 and the reaction was run at room temperature for 4 hours. The yield was 8.6 g and the equivalent weight and water content of the sulfonated copolymer were 871 g/mol and 15%, respectively.

EXAMPLE 13

A solution of 28.5 mL of ClSO$_3$H in 50 mL of chloroform was added over 5 minutes to a stirred solution containing 7.5 g of TFS-m-CF$_3$-TFS copolymer (20% m-CF$_3$-TFS) in 378 mL of chloroform at 60° C. The molar ratio of ClSO$_3$H/monomer unit was 9.8:1 and the reaction was run at 60° C. for 3 hours. A similar workup procedure was used as described in Example 10. The yield was 9.5 g and the equivalent weight and water content of the sulfonated copolymer were 350 g/mol and 776%, respectively.

EXAMPLE 14

7.5 g of TFS-m-CF$_3$-TFS (20% m-CF$_3$-TFS) copolymer was dissolved in 160 mL of chloroform at room temperature. An SO$_3$/O=P(OEt)$_3$ complex containing 13 mL O=P(OEt)$_3$ and 12.4 mL of SO$_3$ in 63.9 mL of chloroform was made at 0° C. and added into the reaction system over 20 seconds. The molar ratio of SO$_3$/O=P(OEt)$_3$ was 4:1 and the molar ratio of SO$_3$/monomer unit was 7:1. The reaction was run at room temperature for 4 hours. The same workup procedure was used as described in Example 10. The yield was 12.8 g and the equivalent weight and water content of the sulfonated copolymer were 379 g/mol and 266%, respectively.

EXAMPLE 15

The same procedure was employed as in Example 14, except that the $SO_3/O{=}P(OEt)_3$ complex was made by adding 11.1 mL of $O{=}P(OEt)_3$ and 10.7 mL of $SO_3$ into 54.8 mL of chloroform (the molar ratio of $SO_3$/monomer unit was 6:1) at 0° C. The yield was 9.9 g and the equivalent weight and water content of the sulfonated copolymer were 399 g/mol and 151%, respectively.

EXAMPLE 16

The same procedure was employed as in Example 14, except that the $SO_3/O{=}P(OEt)_3$ complex was made by adding 10.1 mL of $O{=}P(OEt)_3$ and 9.9 mL of $SO_3$ into 49.8 mL of chloroform (the molar ratio of $SO_3$/monomer unit was 5.6:1) at 0° C. The equivalent weight and water content of the sulfonated copolymer were 437 g/mol and 156%, respectively.

EXAMPLE 17

The same procedure was employed as in Example 14, except that the $SO_3/O{=}P(OEt)_3$ complex was made by adding 7.9 mL of $O{=}P(OEt)_3$ and 7.5 mL of $SO_3$ into 38.7 mL of chloroform (the molar ratio of $SO_3$/monomer unit was 4.2:1) at 0° C. The yield was 12.3 g and the equivalent weight and water content of the sulfonated copolymer were 463 g/mol and 81%, respectively.

EXAMPLE 18

The same procedure was employed as in Example 14, except that the $SO_3/O{=}P(OEt)_3$ complex was made by adding 6.0 mL of $O{=}P(OEt)_3$ and 5.7 mL of $SO_3$ into 29.0 mL of chloroform (the molar ratio of $SO_3$/monomer unit was 3.2:1) at 0° C. The yield was 9.7 g and the equivalent weight and water content of the sulfonated copolymer were 594 g/mol and 42%, respectively.

EXAMPLE 19

The same procedure was employed as in Example 14, except that the $SO_3/O{=}P(OEt)_3$ complex was made by adding 5.0 mL of $O{=}P(OEt)_3$ and 4.7 mL of $SO_3$ into 24.2 mL of chloroform (the molar ratio of $SO_3$/monomer unit was 2.6:1) at 0° C. The yield was 9.1 g and the equivalent weight and water content of the sulfonated copolymer were 825 g/mol and 21%, respectively.

EXAMPLE 20

The same procedure was employed as in Example 14, except that the $SO_3/O{=}P(OEt)_3$ complex was made by adding 4.0 mL of $O{=}P(OEt)_3$ and 3.8 mL of $SO_3$ into 19.4 mL of chloroform (the molar ratio of $SO_3$/monomer unit was 2.1:1) at 0° C. The yield was 8.5 g and the equivalent weight and water content of the sulfonated copolymer were 915 g/mol and 13%, respectively.

EXAMPLE 21

The same procedure was used as in Example 14, except that the $SO_3/O{=}P(OEt)_3$ complex was made by adding 2.0 mL of $O{=}P(OEt)_3$ and 1.9 mL of $SO_3$ into 9.7 mL of chloroform (the molar ratio of $SO_3$/monomer unit was 1.1:1) at 0° C. The yield was 9.1 g and the equivalent weight and water content of the sulfonated copolymer were 31,000 g/mol and 2%, respectively.

EXAMPLE 22

Three sheets of the sulfonated TFS-m-$CF_3$-TFS copolymer membranes were each bonded on opposite major surfaces to two carbon paper electrodes at room temperature under 10,000 pounds of pressure. These membrane electrode assemblies ("MEAs") were tested in the Ballard Mark IV single cell fuel cell (see U.S. Pat. Nos. 4,988,583; 5,108,849; 5,170,124; 5,176,966 and 5,200,278; all incorporated herein by reference in their entirety). The results for the three sulfonated copolymer membranes tested (designated BAM3G01, BAM3G02 and BAM3G03) are shown in Table 1 below.

TABLE 1

Performance of TFS-m-$CF_3$-TFS Copolymer Membranes in Ballard Mark IV Fuel Cell

| Amps/ft² | Cell Voltage (V) | | |
|---|---|---|---|
| | BAM3G01 | BAM3G02 | BAM3G03 |
| 100 | 0.827 | 0.821 | 0.818 |
| 200 | 0.783 | 0.775 | 0.766 |
| 300 | 0.739 | 0.736 | 0.719 |
| 400 | 0.711 | 0.697 | 0.669 |
| 500 | 0.670 | 0.647 | 0.613 |
| 600 | 0.638 | 0.612 | 0.533 |
| 700 | 0.603 | 0.575 | 0.461 |
| 800 | 0.573 | 0.540 | 0.255 |
| 900 | 0.533 | 0.498 | 0.165 |
| 1000 | 0.494 | 0.438 | — |
| 1100 | 0.452 | 0.374 | — |
| 1200 | 0.393 | 0.355 | — |
| 1300 | 0.263 | — | — |

The three sulfonated copolymer membranes tested had the following characteristics:

BAM3G01: Equivalent weight 427; water content 145%; the lifetime of the MEA: 329 hrs at 500 amps/ft²

BAM3G02: Equivalent weight 447; water content 104%; the lifetime of the MEA: 4061 hrs at 500 amps/ft² (gasketed MEA)

BAM3G03: Equivalent weight 470; water content 91%; the lifetime of the MEA: 318 hrs at 500 amps/ft²

The following operation conditions applied to the fuel cell in which the three sulfonated copolymer membranes were tested:

Temperature=70° C., reactant inlet pressure 24 psi for both air and $H_2$, reactant stoichiometries of 2.0 air and 1.15 $H_2$.

FIG. 1 is a polarization plot of voltage as a function of current density in an electrochemical fuel cell employing, respectively, a DuPont Nafion 117 cation exchange membrane, a Dow experimental cation exchange membrane (available under the trade designation XUS 13204.10), and the sulfonated $\alpha,\beta,\beta$-trifluorostyrene copolymeric membrane designated BAM3G01 in Example 22 above. As shown in FIG. 1, the sulfonated $\alpha,\beta,\beta$-trifluorostyrene copolymeric membrane achieved higher cell voltages than the Dow membrane at current densities greater than 800 A/ft². The Dow membrane, in turn, achieved higher cell voltages than the Nafion 117 membrane at all current densities. Furthermore, a sulfonated copolymer of the present invention has exceeded 4000 hours longevity testing in an electrochemical fuel cell test stand.

Copolymers formed from $\alpha,\beta,\beta$-trifluorostyrene (TFS) and m-$CF_3$-$\alpha,\beta,\beta$-trifluorostyrene (m-$CF_3$-TFS) have been produced in yields greater than 80%.

The sulfonated copolymers of the present invention have the following additional advantages:

1. Flexibility to introduce a wide variety of different ion-exchange functionalities due to the presence of the arene groups.
2. The ability to produce a large series of membranes with different equivalent weights starting from the same base copolymer; another flexibility provided by the arene substituents.
3. Processibility, in that these copolymers are soluble in a variety of common solvents, for example, N,N-dimethylformamide, dimethyl sulfoxide and N-methylpyrrolidone.
4. The ability to introduce crosslinking, using conventional techniques, such as those employed in preparing divinylbenzene polystyrene, to enhance physical and mechanical properties.

Crosslinked polymers of the type included in the present invention have the following chemical formula:

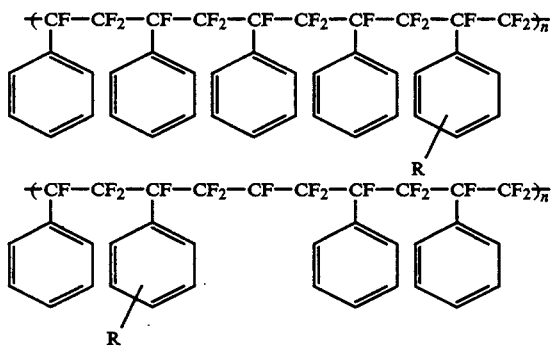

where n is greater than zero and R is fluorine or $CF_3$.

In addition to the utility of the sulfonated copolymeric membranes described herein as ion-exchange membranes for electrochemical fuel cells, the following further utilities are also contemplated:

1. Proton exchange membrane based water electrolysis, which involves a reverse chemical reaction to that employed in hydrogen/oxygen electrochemical fuel cells.
2. Chloralkali electrolysis, typically involving the electrolysis of a brine solution to produce chlorine and sodium hydroxide, with hydrogen as a by-product.
3. Electrode separators in conventional batteries due to the chemical inertness and high electrical conductivity of the sulfonated copolymer membranes.
4. Ion-selective electrodes, particularly those used for the potentiometric determination of a specific ion such as $Ca^{2+}$, $Na^+$, $K^+$ and like ions. These copolymers could also be employed as the sensor material for humidity sensors, as the electrical conductivity of an ion exchange membrane varies with humidity.
5. Ion-exchange material for separations by ion-exchange chromatography. Typical such applications are deionization and desalination of water (for example, the purification of heavy metal contaminated water), ion separations (for example, rare-earth metal ions, trans-uranium elements), and the removal of interfering ionic species.
6. Ion-exchange membranes employed in analytical preconcentration techniques (Donnan Dialysis). This technique is typically employed in analytical chemical processes to concentrate dilute ionic species to be analyzed.
7. Ion-exchange membranes in electrodialysis, in which membranes are employed to separate components of an ionic solution under the driving force of an electrical current. Electrolysis applications include the industrial-scale desalination of brackish water, preparation of boiler feed make-up and chemical process water, de-ashing of sugar solutions, deacidification of citrus juices, separation of amino acids, and the like.
8. Membranes in dialysis applications, in which solutes diffuse from one side of the membrane (the feed side) to the other side according to their concentration gradient. Separation between solutes is obtained as a result of differences in diffusion rates across the membrane arising from differences in molecular size. Such applications include hemodialysis (artificial kidneys) and the removal of alcohol from beer.
9. Membranes in gas separation (gas permeation) and pervaporation (liquid permeation) techniques.
10. Bipolar membranes employed in water splitting and subsequently in the recovery of acids and bases from waste water solutions.

While particular elements, embodiments and applications of the present invention have been shown and described, it will be understood, of course, that the invention is not limited thereto since modifications may be made by those skilled in the art, particularly in light of the foregoing teachings. It is therefore contemplated by the appended claims to cover such modifications as incorporate those features which come within the spirit and scope of the invention.

What is claimed is:

1. A polymeric composition comprising:

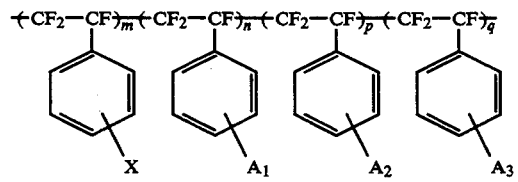

where m is an integer greater than zero and at least one of n, p and q is an integer greater than zero; $A_1$, $A_2$ and $A_3$ are selected from the group consisting of alkyls, halogens, $C_yF_{2y+1}$ where y is an integer greater than zero, O-R (where R is selected from the group consisting of alkyls, perfluoroalkyls and aryls), $CF=CF_2$, CN, $NO_2$ and OH; and X is selected from the group consisting of $SO_3H$, $PO_3H_2$, $CH_2PO_3H_2$, COOH, $OSO_3H$, $OPO_3H_2$, $OArSO_3H$ where Ar is an aromatic, $NR_3^+$ (where R is selected from the group consisting of alkyls, perfluoroalkyls and aryls) and $CH_2NR_3^+$ (where R is selected from the group consisting of alkyls, perfluoroalkyls and aryls).

2. The polymeric composition of claim 1 wherein adjacent polymers are crosslinked.

3. The polymeric composition of claim 1 wherein the group from which $A_1$, $A_2$ and $A_3$ are selected further consists of SO$_3$H, PO$_3$H$_2$, CH$_2$PO$_3$H$_2$, COOH, OSO$_3$H, OPO$_3$H$_2$, OArSO$_3$H where Ar is an aromatic, NR$_3^+$ (where R is selected from the group consisting of alkyls, perfluoroalkyls and aryls) and CH$_2$NR$_3^+$ (where R is selected from the group consisting of alkyls, perfluoroalkyls and aryls), at least one of A$_1$, A$_2$ and A$_3$ is selected from the group consisting of SO$_3$H, PO$_3$H$_2$, CH$_2$PO$_3$H$_2$, COOH, OSO$_3$H, OPO$_3$H$_2$, OArSO$_3$H where Ar is an aromatic, NR$_3^+$ (where R is selected from the group consisting of alkyls, perfluoroalkyls and aryls) and CH$_2$NR$_3^+$ (where R is selected from the group consisting of alkyls, perfluoroalkyls and aryls), and wherein A$_1$, A$_2$ and A$_3$, when present, are each group members other than X.

4. A polymeric composition consisting essentially of:

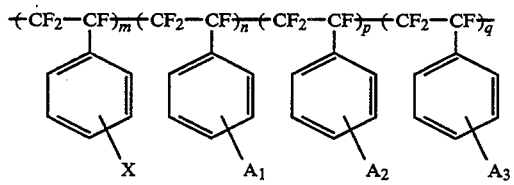

where m is an integer greater than zero and at least one of n, p and q is an integer greater than zero; A$_1$, A$_2$ and A$_3$ are selected from the group consisting of alkyls, halogens, C$_y$F$_{2y+1}$ where y is an integer greater than zero, O-R (where R is selected from the group consisting of alkyls, perfluoroalkyls and aryls), CF=CF$_2$, CN, NO$_2$ and OH; and X is selected from the group consisting of SO$_3$H, PO$_3$H$_2$, CH$_2$PO$_3$H$_2$, COOH, OSO$_3$H, OPO$_3$H$_2$, OArSO$_3$H where Ar is an aromatic, NR$_3^+$ (where R is selected from the group consisting of alkyls, perfluoroalkyls and aryls) and CH$_2$NR$_3^+$ (where R is selected from the group consisting of alkyls, perfluoroalkyls and aryls).

5. The polymeric composition of claim 4 wherein adjacent polymers are crosslinked.

6. The polymeric composition of claim 4 wherein the group from which A$_1$, A$_2$ and A$_3$ are selected further consists of SO$_3$H, PO$_3$H$_2$, CH$_2$PO$_3$H$_2$, COOH, OSO$_3$H, OPO$_3$H$_2$, OArSO$_3$H where Ar is an aromatic, NR$_3^+$ (where R is selected from the group consisting of alkyls, perfluoroalkyls and aryls) and CH$_2$NR$_3^+$ (where R is selected from the group consisting of alkyls, perfluoroalkyls and aryls), at least one of A$_1$, A$_2$ and A$_3$ is selected from the group consisting of SO$_3$H, PO$_3$H$_2$, CH$_2$PO$_3$H$_2$, COOH, OSO$_3$H, OPO$_3$H$_2$, OArSO$_3$H where Ar is an aromatic, NR$_3^+$ (where R is selected from the group consisting of alkyls, perfluoroalkyls and aryls) and CH$_2$NR$_3^+$ (where R is selected from the group consisting of alkyls, perfluoroalkyls and aryls), and wherein A$_1$, A$_2$ and A$_3$, when present, are each group members other than X.

7. A polymeric composition comprising:

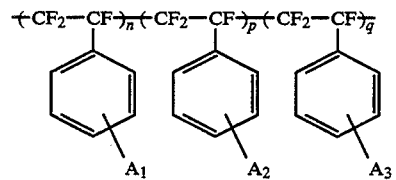

where at least one of n, p and q is an integer greater than zero; and A$_1$, A$_2$ and A$_3$ are selected from the group consisting of O-R (where R is selected from the group consisting of C$_y$H$_{2y+1}$ and C$_y$F$_{2y+1}$, where y is an integer greater than three, and aryls), CF=CF$_2$, CN, NO$_2$ and OH.

8. A polymeric composition consisting essentially of:

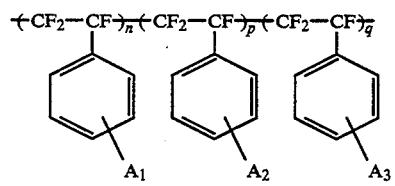

where at least one of n, p and q is an integer greater than zero; and A$_1$, A$_2$ and A$_3$ are selected from the group consisting of O-R (where R is selected from the group consisting of C$_y$H$_{2y+1}$ and C$_y$F$_{2y+1}$, where y is an integer greater than three, and aryls), CF=CF$_2$, CN, NO$_2$ and OH.

* * * * *

UNITED STATES PATENT AND TRADEMARK OFFICE
CERTIFICATE OF CORRECTION

PATENT NO. : 5,422,411
DATED : June 6, 1995
INVENTOR(S) : Wei, et. al.

It is certified that error appears in the above-indentified patent and that said Letters Patent is hereby corrected as shown below:

Title page, col. 2, under Other Publications, line 2, change "fluoroalkenylzine" to -- fluoroalkenylzinc--.

Drawings:
Under the drawing, insert--FIG. 1--.
Column 6, line 26, delete "." after the word "set".--.
Column 9, lines 25-40: the chemical formula should read--

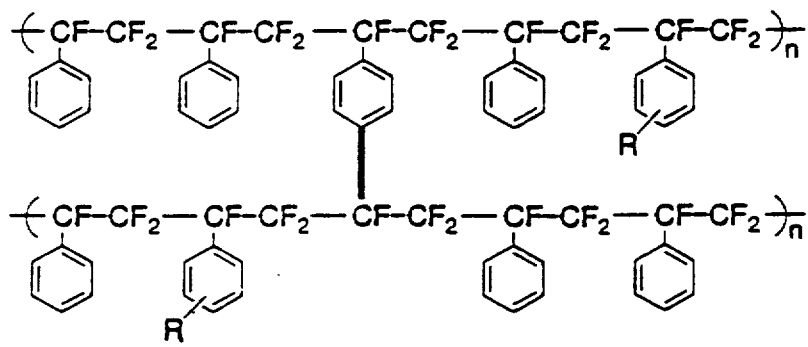

Signed and Sealed this

Ninth Day of April, 1996

Attest:

BRUCE LEHMAN

Attesting Officer

Commissioner of Patents and Trademarks